(12) United States Patent
Lee

(10) Patent No.: US 6,848,907 B2
(45) Date of Patent: Feb. 1, 2005

(54) SCREW FOR DENTAL IMPLANTS

(75) Inventor: Jae-Bong Lee, Haengwon (KR)

(73) Assignee: Osstem Implant Co., Ltd., Busan (KR)

( * ) Notice: Subject to any disclaimer, the term of this patent is extended or adjusted under 35 U.S.C. 154(b) by 162 days.

(21) Appl. No.: 10/179,637

(22) Filed: Jun. 24, 2002

(65) Prior Publication Data

US 2003/0235801 A1 Dec. 25, 2003

(51) Int. Cl.$^7$ .............................. A61C 8/00; F16B 23/00
(52) U.S. Cl. ...................... 433/173; 433/174; 411/403
(58) Field of Search .................................. 433/172, 173, 433/174, 175, 176; 411/402, 403, 404, 410

(56) References Cited

U.S. PATENT DOCUMENTS

| | | | |
|---|---|---|---|
| 391,097 A | * 10/1888 | Thayer | |
| 3,604,305 A | * 9/1971 | Dreger | |
| 4,790,753 A | 12/1988 | Fradera | |
| 5,358,368 A | * 10/1994 | Conlan et al. | 411/410 |
| 5,407,359 A | 4/1995 | Balfour et al. | |
| 5,439,380 A | * 8/1995 | Marlin | 433/172 |
| 6,364,664 B1 | * 2/2002 | Watanabe | 433/174 |
| 2003/0053887 A1 | * 3/2003 | Brooks | 411/403 |

OTHER PUBLICATIONS

An article entitled "Custom–made Cover Screws to Fit . . . ", by Howell, Jr., et al., published By The Journal of Prosthetic Dentistry, Aug. 1997, vol. 78, pp. 209–211.
An article entitled "Preventing Loosening of Implant Abutment Screws", By Cavazos, Jr., et al., published by The Journal of Prosthetic Dentistry, (1996), vol. 75, No. 5, pp. 566–569.

* cited by examiner

Primary Examiner—Cary E. O'Connor
(74) Attorney, Agent, or Firm—Bachman & LaPointe, P.C.

(57) ABSTRACT

A screw for dental implants, used to fix dental prostheses to abutments combined with fixtures previously inserted in the alveolar bone, includes a screw portion and a screw-head portion. The screw-head portion includes a pair of inclined planes on either side of a center line, wherein the inclined planes form a V-character shape when seen from the side along a center line, each forming at a predetermined angle with respect to a plane perpendicular to the axis of the screw and a tool-receiver, formed between the inclined planes along a center line crossing an upper face of the screw, for transmitting working torque exerted by a tool. A screw set for dental implants includes a plurality of dental-implant screws, each having a screw portion and a screw-head portion of varying height, and each screw-head portion includes the same combination of guide and tool-receiver. The improved screw facilitates tightening and untightening of the screw.

12 Claims, 5 Drawing Sheets

--Fig. 1--

Contemporary Art

Contemporary Art

--Fig. 5--
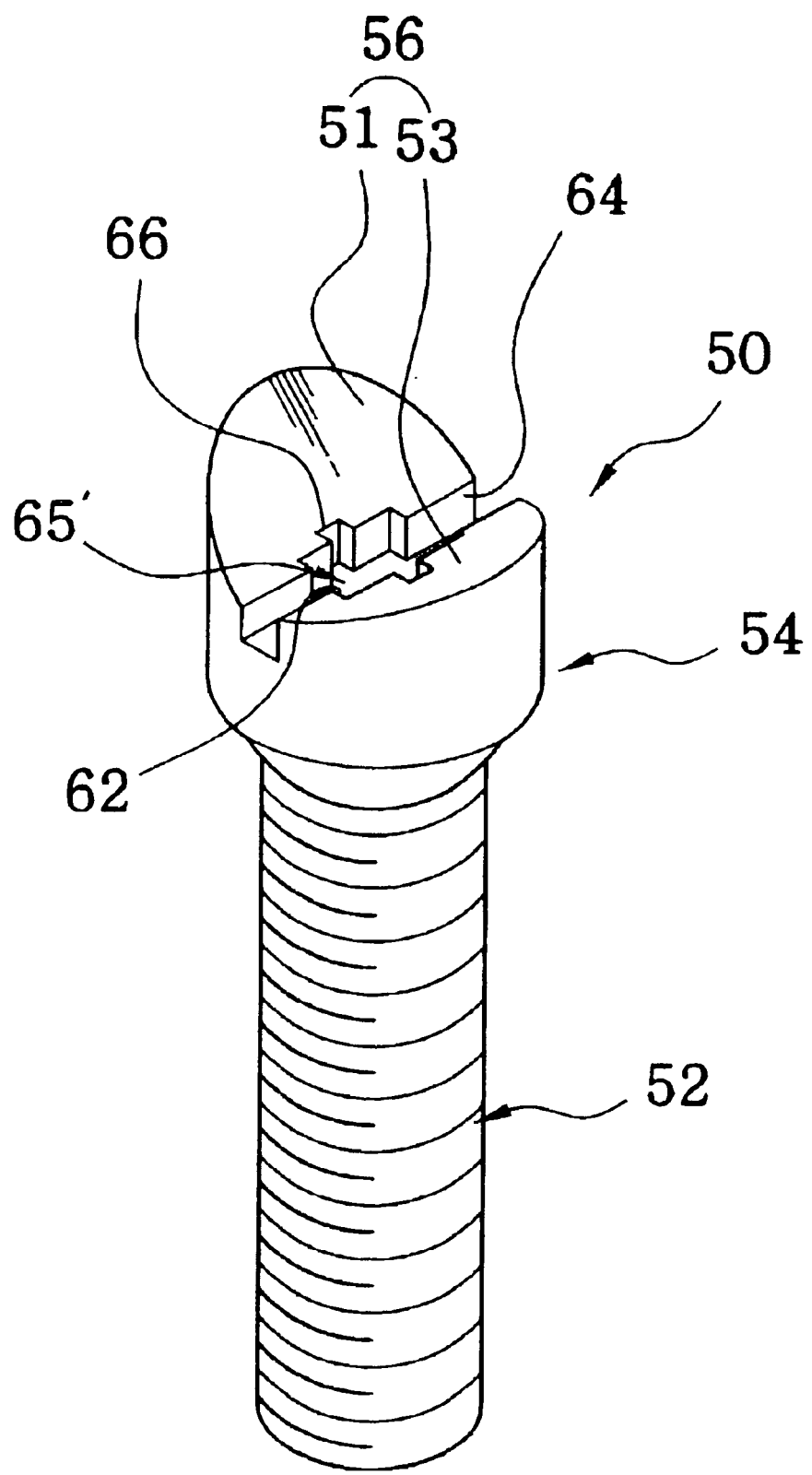

SCREW FOR DENTAL IMPLANTS

BACKGROUND OF THE INVENTION

1. Field of the Invention

The present invention relates to a screw for dental implants and, more particularly, to an improved screw for dental implants, used for fitting dental prostheses by tightening to abutments combined with fixtures previously inserted in alveolar bones and facilitating manipulation of the screw.

2. Discussion of the Related Art

FIG. 1 is a side view of a screw for dental implants in accordance with a contemporary art. FIG. 2 is a longitudinal cross-sectional view of a screw for dental implants shown in FIG. 1, wherein the screw is shown in a tightened state of use with respect to associative components.

Referring to FIGS. 1 and 2, a dental-implant screw 2 is a screw used for fitting a dental prosthesis 10 to an abutment 8. The abutment 8 is coupled to a fixture 6, which has been coupled with an alveolar bone 4.

The fixture 6 comprises a knurled portion 12 inserted as an anchor into the alveolar bone 4, a fixing hole 14 formed to prevent the fixture 6 from moving above the upper end of the knurled portion 12, and a first female-threaded portion 16 to receive the abutment 8.

The abutment 8 comprises a first male-threaded portion 18 formed at the lower end thereof and screwed into the first female-threaded portion 16 of the fixture 6, and a body portion 20 tapered to facilitate the fitting of the dental prosthesis 10. Further, the body portion 20 of the abutment 8 comprises a second female-threaded portion 22 for receiving the screw 2.

The screw 2 comprises a second male-threaded portion 24, formed to be inserted into the second female-threaded portion 22, and a screw-head portion 28 having a recess 26 to be manipulated using a tool such as a screwdriver.

The upper face of the screw-head portion 28 of the screw 2 is formed as a flat plane, and the recess 26 of the screw-head portion 28 is formed as a hexagon, a rectangle, or a slot-shape to be tightened by the tool.

The screw 2 is coupled to the abutment 8 via a penetration hole 30 formed in the dental prosthesis 10, so that the dental prosthesis 10 is fixed firmly.

To tighten the screw 2 in the penetration hole 30, the tip of the tool should fit in the recess 26 to enable the screw 2 to be turned by force. Due to the complex shapes of dental prostheses and spatial restrictions of the oral cavity, however, fitting the tool in the recess is difficult and manipulating the tool within the limited space is cumbersome.

In other words, since the space of the oral cavity is very limited, it is difficult to fit the tool into the recess 26 of the screw-head portion 28 of the screw 2 inserted in the penetration hole 30 formed in the dental prosthesis 10. Thus, repeated attempts to fit the tool in the recess 26 and turn the screw 2 are often necessary, because the upper face of the screw-head portion is flat. Accordingly, the tool cannot be guided into the recess 26, and on occasion, slides off the upper face. As a result, the screw 2 cannot be tightened promptly, and when tightened by an immoderate torque, the surrounding portions of the recess 26 are easily dulled by the tool.

The conventional screw for dental implants exhibits several further disadvantages: when inserted in the penetration hole 30 of the dental prosthesis 10, the screw 2 is difficult to locate visually, which hinders manipulation of the screw 12; if the surrounding portions of the recess 26 of the screw 2 become dull, the screw can be untightened only after breaking down the dental prosthesis 10, which necessitates remaking the dental prosthesis 10; the reduction of the clamping force of a tightened screw 2, due to the normal masticatory operation of the dental prosthesis 10, results in a loosening of the dental prosthesis, allowing undue movement; and a repetitive manipulation of the screw 2, e.g., tightening and untightening, is required for regular cleaning of the fitted dental prosthesis 10, but in retightening the screw 2 after a cleaning operation, the required clamping force is difficult to achieve if the tightening and untightening have been performed by compulsion, such that the surrounding portions of the recess 26 of the screw 2 become dull.

SUMMARY OF THE INVENTION

Accordingly, the present invention has been devised in order to overcome the foregoing disadvantages.

It is an object of the present invention to provide an improved screw for dental implants used for fixing dental prostheses to abutments combined with fixtures previously inserted in alveolar bones and facilitating manipulation of the screw.

It is a further object of the present invention to provide a set of improved screws for dental implants, each consisting of a plurality of dental-implant screws, wherein the height of each screw-head portion varies in accordance with the shape and size of dental prostheses for alternative use and for easy identification of the screw in the limited oral cavity.

In order to achieve the foregoing objects, the present invention provides a screw for dental implants, having a screw portion and a screw-head portion, said screw-head portion comprising a pair of inclined planes on either side of a center line, wherein the inclined planes form a V-character shape when seen from the side along a center line; and tool-receiving means, formed between the inclined planes along the center line crossing an upper face of the screw, for transmitting working torque exerted by a tool.

Each of the inclined planes of the tool-receiving means forms an angle of 30° to 40° with respect to a plane perpendicular to the axis of the screw. A plurality of recesses is formed in the tool-receiving means, each recess having a unique shape with respect to the remainder of the plurality.

The tool-receiving means may comprise a hexagonal recess, a rectangular recess, and a slot-shaped recess or a rectangular recess, a slot-shaped recess, and a cross-shaped recess. Other combinations of recess shapes are possible according to the principles of the present invention.

The present invention further provides a screw set for dental implants comprising a plurality of dental-implant screws, each having a screw portion and a screw-head portion, wherein each screw-head portion comprises a pair of inclined planes on either side of a center line, wherein the inclined planes form a V-character shape when seen from the side along a center line, each forming at a predetermined angle with respect to a plane perpendicular to the axis of the screw; and tool-receiving means, formed between the inclined planes along a center line crossing an upper face of the screw, for transmitting working torque exerted by a tool.

The height of the screw-head portion of each dental-implant screw varies, at regular intervals, over a range from 1.5 mm to 12 mm. Each interval is 1 mm to 2 mm in size.

BRIEF DESCRIPTION OF THE DRAWINGS

The above and other objects, features, and advantages of the present invention will be more clearly understood from the following detailed description taken in conjunction with the accompanying drawings, in which:

FIG. 5 is a perspective view of a screw for dental implants in accordance with another embodiment of the present invention.

DETAILED DESCRIPTION OF THE PREFERRED EMBODIMENTS

Figure 1:
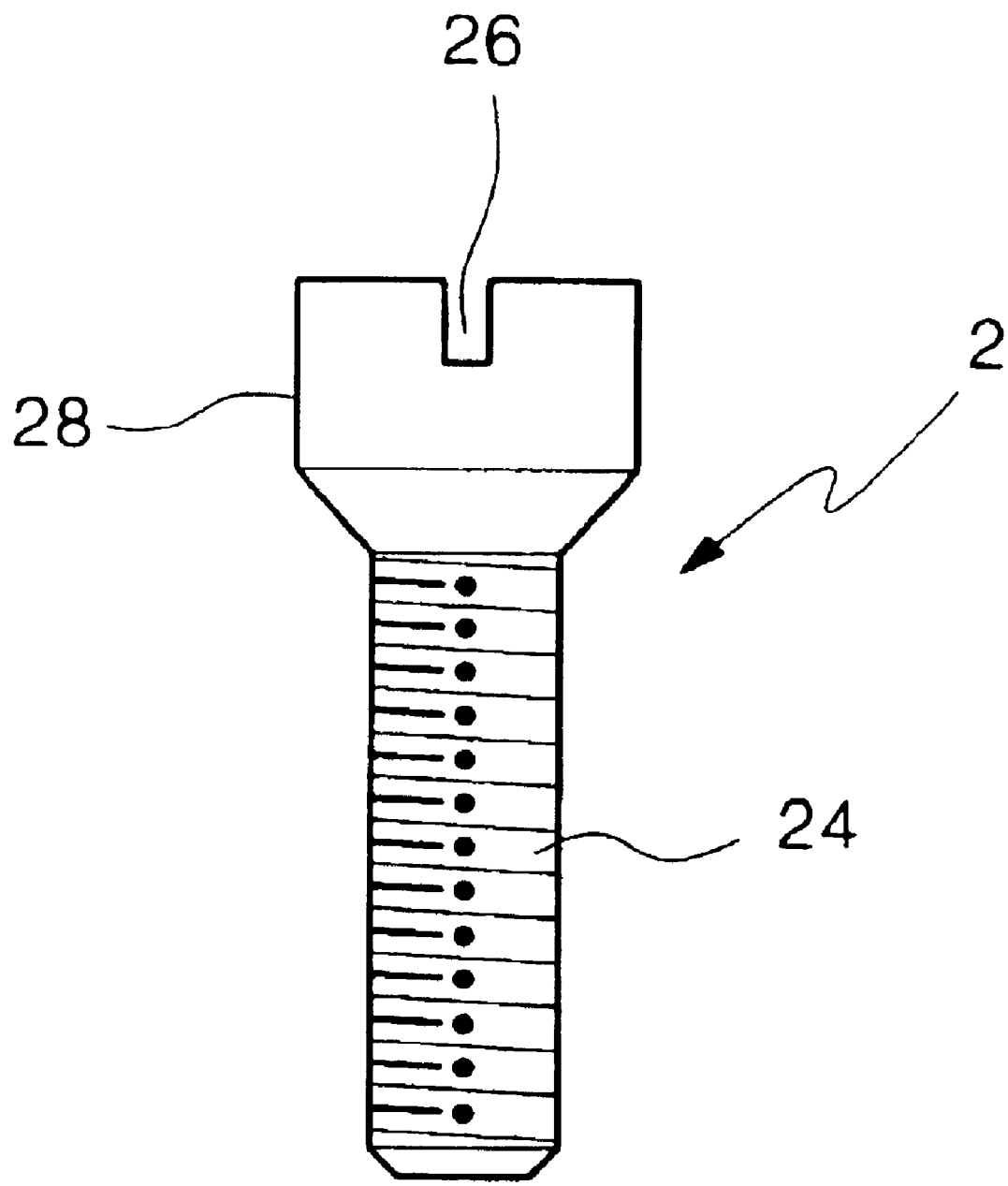
FIG. 1 is a side view of a screw for dental implants in accordance with a contemporary art.
Figure 2:
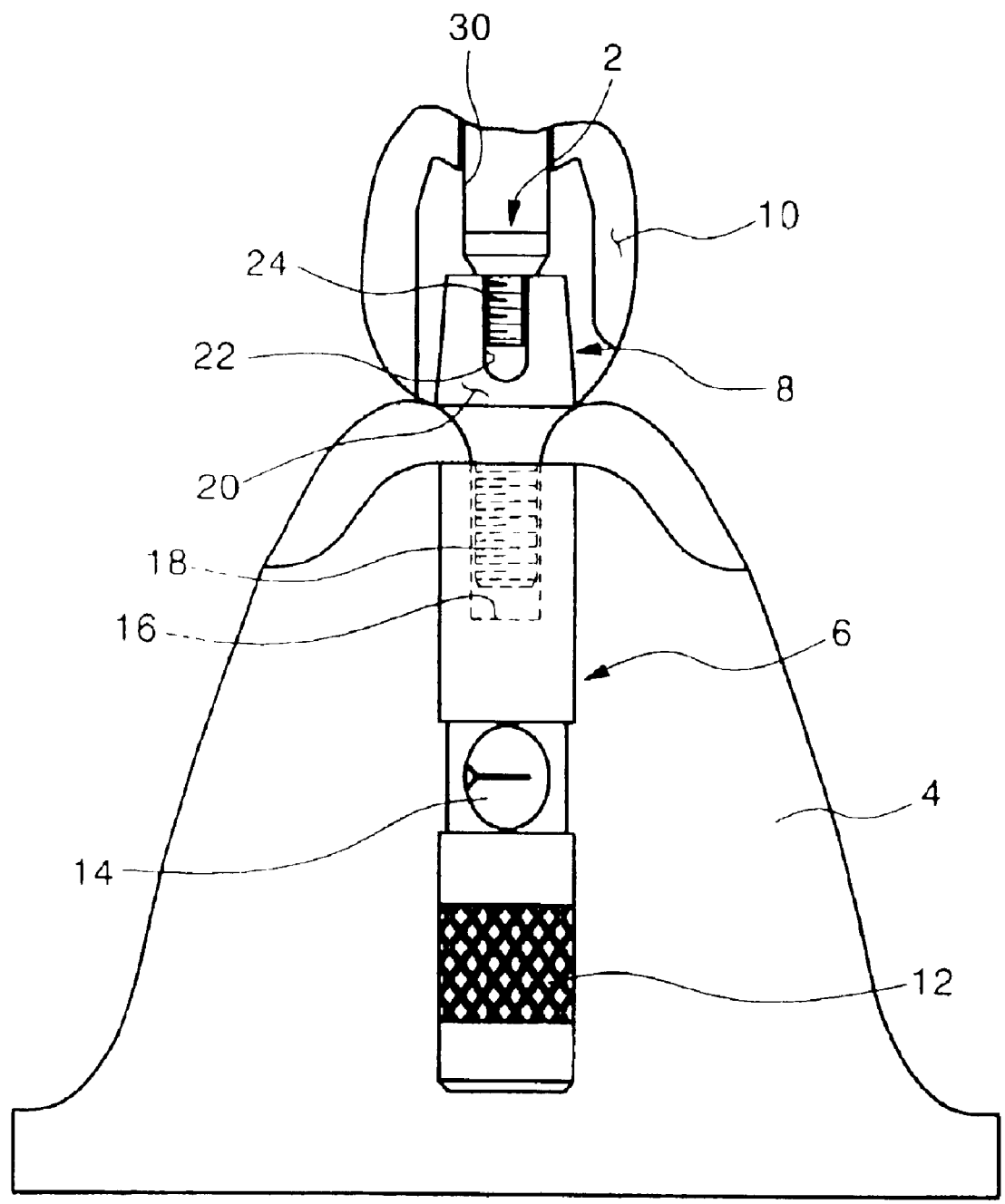
FIG. 2 is a longitudinal cross-sectional view of the screw for dental implants of FIG. 1, with the screw shown in a tightened state of use with respect to associative components.
Figure 3:
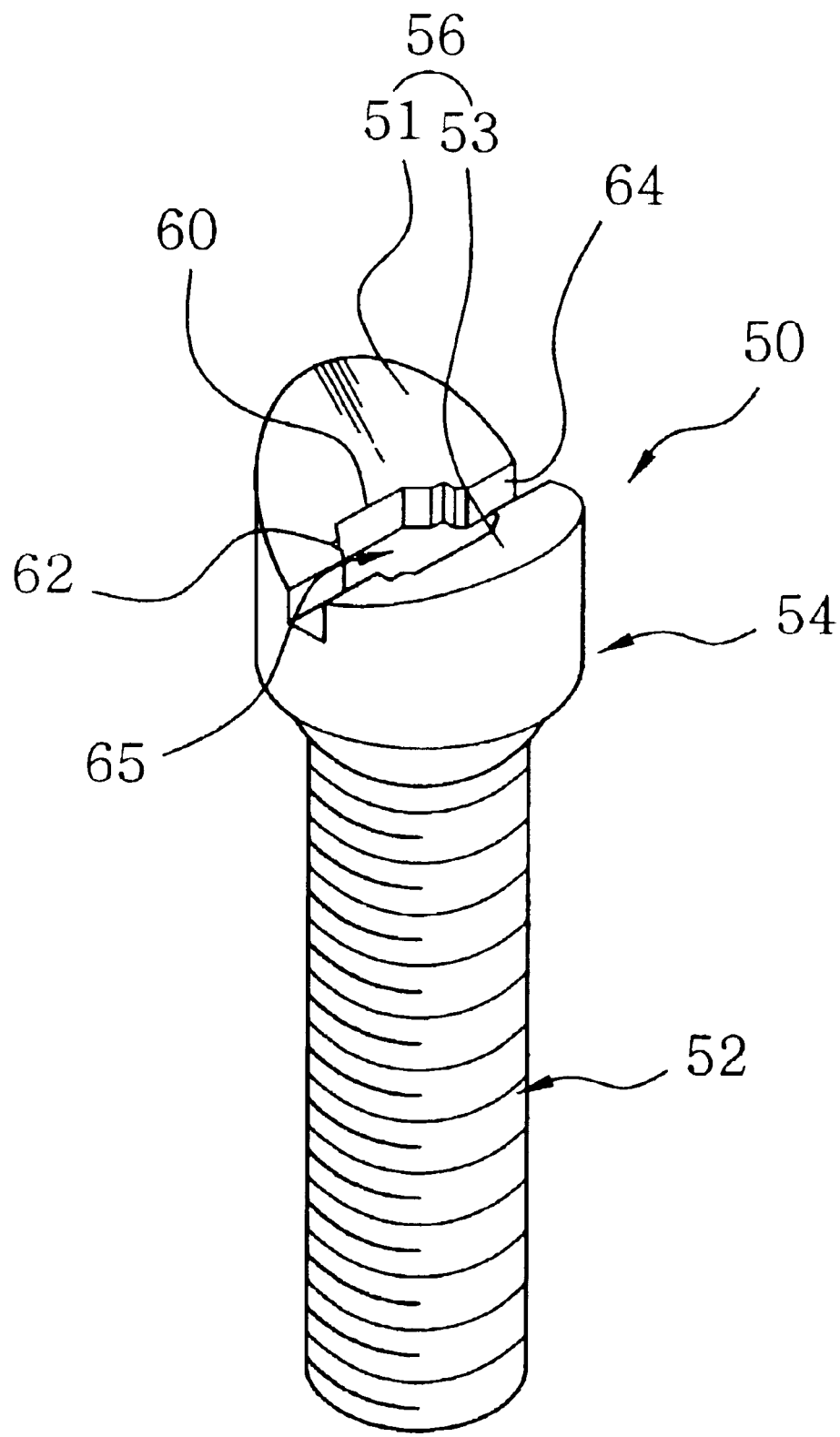
FIG. 3 is a perspective view of a screw for dental implants in accordance with the present invention.
Figure 4:
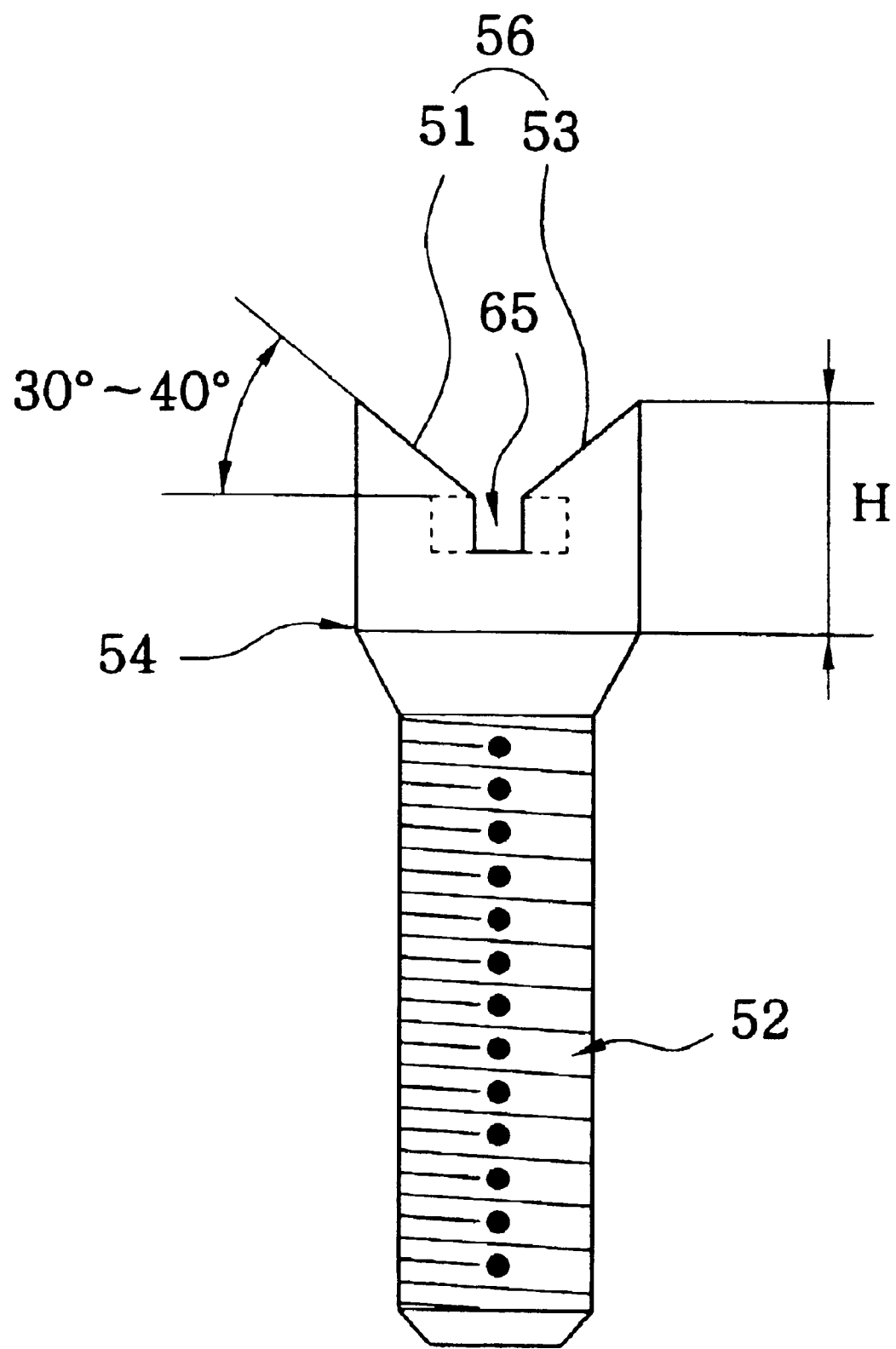
FIG. 4 is an elevational side view of a screw for dental implants of FIG. 3.

Referring to FIGS. 3 and 4, a screw 50 for dental implants comprises a screw portion 52 and a screw-head portion 54. The screw-head portion 54 comprises a guide means 56 consisting of a pair of inclined planes 51 and 53 of a predetermined angle, which are symmetrical with respect to each other along a center line crossing the upper face of the screw 50. The screw-head portion 54 further comprises a tool-receiving means 65 formed between the inclined planes 51 and 53 along a center line crossing the upper face of the screw 50.

The predetermined angle of each of the inclined planes 51 and 53 is preferably 30° to 40° with respect to a plane perpendicular to the axis of the screw.

Accordingly, the tip of a tool (not shown) for manipulating the screw 50 is guided during insertion by being slid on the inclined planes 51 and 53. Thus, as the tool is inserted into the screw 50, the tool becomes seated in the tool-receiving means 65.

The tool-receiving means 65 comprises a plurality of recesses wherein each recess has a unique shape with respect to the remainder of the plurality. For example, as shown in FIG. 3, the tool-receiving means 65 is formed as a single integrated recess consisting of a hexagonal recess 60, a rectangular recess 62, and a slot-shaped recess 64, or, as shown in FIG. 5, as a single integrated recess 65' consisting of a rectangular recess 62, a slot-shaped recess 64, and a cross-shaped recess 66. Various types of recesses for receiving the tool are formed integrally on the same screw-head portion 54. Accordingly, localized abrasion of the tool-receiving means 65 can be reduced and alternative tools can be used for manipulating the same screw.

In other words, the screw 50 for dental implants of the present invention comprises a tool-receiving means 65 consisting of a plurality of recesses selected from a group comprising the hexagonal recess 60, rectangular recess 62, slot-shaped recess 64, and cross-shaped recess 66 on the screw-head portion 54, where each recess receives a different shape of tool. Accordingly, work is facilitated by an increased choice of tools and since alternative tools can be used if one or more of the recesses is unusable due to excessive wear. Therefore, even in a situation where a portion of the available recesses of the screw 50 is unusable due to excessive wear caused by repetitive loosening and tightening in the process of regular cleaning, an alternative tool may be utilized, allowing continued manipulation of the screw 50 without breaking down the dental prosthesis.

Since the screw-head portion 54 of the screw 50 comprises the guide means 56 consisting of the inclined planes 51 and 53, the tip of the tool is easily fit into the correspondingly shaped recess upon insertion. Thus, the number of attempts by the operator to fit the tool into the tool-receiving means 65 is reduced, which facilitates the whole working process.

The present invention further provides a set of dental-implant screws, comprising a plurality of the screws 50 for dental implants in accordance with the embodiments described above.

More particularly, the screw set for dental implants comprises a plurality of the screws 50 for dental implants, wherein a height H of the screw-head portion 54 of each screw 50 varies.

The height H of the screw-head portion of each screw 50 varies from 1.5 mm to 12 mm, in regular intervals of from 1 mm to 2 mm, and preferably 1 mm or 2 mm, thus constituting a screw set comprising from five to ten different screws. Providing a screw set comprising various kinds of screws, each with a different height dimension for the screw-head portion, the present invention allows use of a screw of the proper dimension, which is readily distinguishable from the operator's perspective while fixing a dental prosthesis to an abutment.

As stated above, the screw set in accordance with the present invention comprises a plurality of screws 50 wherein the height dimension of the screw-head portion 54 of each screw 50 varies, to ensure that alternative screws can be used depending on the shapes and sizes of dental prostheses to be fixed, and thus enables effective manipulation of the screw by using a tool while performing work in a limited space.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. A screw for dental implants, having a screw portion and a screw-head portion, said screw-head portion comprising:

a substantially non-horizontal upper surface formed by a pair of inclined planes on either side of a center line, wherein the inclined planes form a V-character shape when seen from the side along the center line, each forming a predetermined angle with respect to a plane perpendicular to the axis of the screw; and tool-receiving means formed between the inclined planes along the center line for transmitting working torque exerted by a tool.

2. The screw for dental implants according to claim 1, wherein the predetermined angle is between 30° and 40°.

3. The screw for dental implants according to claim 1, wherein a plurality of recesses is formed in said tool-receiving means, each recess having a unique shape with respect to the remainder of the plurality.

4. The screw for dental implants according to claim 1, wherein three recesses are formed in said tool-receiving means.

5. The screw for dental implants according to claim 4, wherein the recesses formed in said tool-receiving means are hexagonal, rectangular, and slot-shaped, respectively.

6. The screw for dental implants according to claim 4, wherein the recesses formed in said tool-receiving means are rectangular, slot-shaped, and cross-shaped, respectively.

7. A screw set for dental implants comprising:
- a plurality of dental-implant screws, each having a screw portion and a screw-head portion, wherein each screw-head portion of said plurality of dental-implant screws comprises:
- a substantially non-horizontal upper surface formed by a pair of inclined planes on either side of a center line, wherein the inclined planes form a V-character shape when seen from the side along the center line, each forming at a predetermined angle with respect to a plane perpendicular to the axis of the screw; and
- tool-receiving means formed between the inclined planes along the center line for transmitting working torque exerted by a tool, and wherein the height of each screw-head portion varies with respect to the remainder of the screw-head portions of said plurality.

8. The screw set for dental implants according to claim 7, wherein the height of each screw-head portion ranges from 1.5 mm to 12 mm.

9. The screw set for dental implants according to claim 8, wherein the height of each screw-head portion varies within the range at a regular interval.

10. The screw set for dental implants according to claim 9, wherein the regular interval is from 1 mm to 2 mm.

11. The screw set for dental implants according to claim 10, wherein the regular interval is 1 mm.

12. The screw set for dental implants according to claim 10, wherein the regular interval is 2 mm.

* * * * *